United States Patent [19]

Lesher et al.

[11] 3,960,945

[45] June 1, 1976

[54] 4-[-(ALKOXY OR POLYHALOALKOXY)-BENZAMIDO]CYCLOHEXANONES

[75] Inventors: George Y. Lesher, Rensselaer; Karl O. Gelotte, Nassau; Alexander R. Surrey, Albany, all of N.Y.

[73] Assignee: Sterling Drug Inc., New York, N.Y.

[22] Filed: Feb. 24, 1975

[21] Appl. No.: 552,162

Related U.S. Application Data

[63] Continuation-in-part of Ser. No. 462,388, April 19, 1974, Pat. No. 3,901,920.

[52] U.S. Cl............... 260/559 R; 260/340.7; 260/563 R; 260/570.9; 424/278
[51] Int. Cl.$^2$........................... C07C 103/26
[58] Field of Search .................. 260/559 R

[56] References Cited
UNITED STATES PATENTS

| | | |
|---|---|---|
| 3,352,884 | 11/1967 | Fonken et al............. 260/553 D X |
| 3,840,598 | 10/1974 | Lesher .................... 260/559 R |
| 3,869,443 | 3/1975 | Lesher .................... 260/559 R X |

OTHER PUBLICATIONS
Bretschneider et al., Monetsh. Chem. 1972, 103(5), pp. 1380–1382.

*Primary Examiner*—Robert V. Hines
*Assistant Examiner*—Thomas A. Waltz
*Attorney, Agent, or Firm*—Robert K. Bair; B. Woodrow Wyatt

[57] ABSTRACT

3-R-3-($Ac_2$NH)-9-R'-9-($Ac_1$NH)-1,5-dioxaspiro[5.5]undecane (I), where R and R' are each hydrogen or lower-alkyl, $Ac_1$ is lower-alkanoyl or 4-$Q_1$-benzoyl and $Ac_2$ is 4-$Q_2$-benzoyl where $Q_1$ and $Q_2$ each is lower-alkoxy or polyhalo-lower-alkoxy, are antifertility agents. The compounds are prepared by di-acylating 3-R-9-R'-1,5-dioxaspiro[5.5]undecan-3,9-diamine (II) or mono-acylating 9-($Ac_1$NH)-3-R-9-R'-1,5-dioxaspiro[5.5]undecan-3-amine (IV). IV and II are prepared by oxidizing 4-($Ac_1$NH)-4-R'-cyclohexanol (VI) to produce 4-($Ac_1$NH)-4-R'-cyclohexanone (VII), reacting VII with 2-$NO_2$-2-R-1,3-propanediol to produce 3-R-3-$NO_2$-9-($Ac_1$NH)-9-R'-1,5-dioxaspiro[5.5]undecane (VIII), reducing VIII to produce the corresponding 3-amine (IV) and hydrolyzing IV to the corresponding 3,9-diamine (II). Methods of preparing VI are shown.

4 Claims, No Drawings

4-[-(ALKOXY OR POLYHALOALKOXY)-BENZAMIDO]CYCLOHEXANONES

CROSS-REFERENCE TO RELATED APPLICATIONS

This application is a continuation-in-part of the copending application Ser. No. 462,388, filed Apr. 19, 1974 and now U.S. Pat. No. 3,901,920 issued Aug. 26, 1975, which discloses and claims 3-R-3-($Ac_2NH$)-9-R'-9-($Ac_1NH$)-1,5-dioxaspiro[5.5]undecanes (I) and also discloses, as intermediates, the instantly claimed 4-($Ac_3NH$)-4-R'-cyclohexanones (X), which are also disclosed as intermediates in copending application Ser. No. 462,389, filed Apr. 19, 1974 and now U.S. Pat. No. 3,895,036 issued July 15, 1975, which discloses and claims intermediates designated herein as II and IV only where $Ac_1$ is lower-alkanoyl and VIII only where $Ac_1$ is lower-alkanoyl.

BACKGROUND OF THE INVENTION

1. Field of the Invention

This invention relates to certain 4-[4-(alkoxy or polyhaloalkoxy)-benzamido]cyclohexanones which are useful as intermediates in the preparation of certain 1,5-dioxaspiro[5.5]-undecane derivatives (I), which are useful as antifertility agents.

2. Description of the Prior Art

The Upjohn Co. Fonken et al. U.S. Pat. No. 3,352,884, issued Nov. 14, 1967, shows the microbiological oxygenation of N-cyclohexylbenzamide to produce N-(4-hydroxycyclohexyl)benzamide (Example 13) and its oxidation to produces N-(4-oxocyclohexyl)-benzamide (Example 20), i.e., alternatively named as 4-benzamidocyclohexanone. The benzamido moiety in this compound is first reduced to benzyl using lithium aluminum hydride (Example 22) and the benzyl group removed by catalytic hydrogenation to produce 4-hydroxycyclohexylamine (Example 23).

SUMMARY OF THE INVENTION

In its composition aspect, the invention relates to 4-($Ac_3NH$)-4-R'-cyclohexanones (X) where R' is hydrogen or lower-alkyl, $Ac_3$ is 4-$Q_1$-benzoyl with $Q_1$ being lower-alkoxy or polyhalo-lower-alkoxy. These compounds are useful as intermediates in the preparation of antifertility agents (I).

The invention in its process aspects resides in the two-step combination and the latter step of the process which comprises reacting 4-amino-4-R'-cyclohexanol with a 4-$Q_1$-benzoylating agent to produce 4-(4-$Q_1$-benzamido)-4-R'-cyclohexanol (IX) and reacting IX with an oxidizing agent capable of converting secondary alcohols to ketones to produce X.

DETAILED DESCRIPTION INCLUSIVE OF PREFERRED EMBODIMENTS

The composition aspect of the invention resides in 4-($Ac_3NH$)-4-R'-cyclohexanones of the formula X

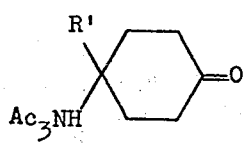

X where R' is hydrogen or lower-alkyl and $AC_3$ is 4-$Q_1$-benzoyl, $Q_1$ being lower-alkoxy or polyhalo-lower-alkoxy. Preferred embodiments of X are the compounds where R' is hydrogen and $Ac_3$ is 4-methoxybenzoyl or 4-trifluoromethoxybenzoyl. The compounds of formula X are useful as intermediates in the preparation of 3-R-3-($Ac_2NH$)-9-R'-9-($Ac_3NH$)-1,5-dioxaspiro[5.5]undecanes (I') where R and R' are each hydrogen or lower-alkyl, $Ac_2$ is 4-$Q_2$-benzoyl, $Ac_3$ is 4-$Q_1$-benzoyl, $Q_1$ and $Q_2$ each being lower-alkoxy or polyhalo-lower-alkoxy. The said 1,5-dioxaspiro[5.5]undecanes (I') are useful as antifertility agents.

Process aspects of the invention for preparing the compounds of formula X resides in the two-step combination and the latter step of the process which comprises reacting 4-amino-4-R'-cyclohexanol, where R' is hydrogen or lower-alkyl, with a 4-$Q_1$-benzoylating agent, where $Q_1$ is lower-alkoxy or polyhalo-lower-alkoxy, to produce 4-(4-$Q_1$-benzamido)-4-R'-cyclohexanol and reacting said cyclohexanol with an oxidizing agent capable of converting secondary alcohols to ketones to produce 4-(4-$Q_1$-benzamido)-4-R'-cyclohexanone.

"Lower-alkyl", as used herein, e.g., as one of the meanings for R' in formula X hereinabove and as one of the meanings for R or R' in formula I hereinbelow, is an alkyl radical, preferably having from one to four carbon atoms, which can be arranged as straight or branched chains including, for instance, but without limiting the generality of the foregoing, methyl, ethyl, n-propyl, isopropyl, n-butyl sec-butyl, isobutyl and tert-butyl.

"Lower-alkoxy", as used herein, e.g., as one of the meanings for $Q_1$ in the definition of $Ac_3$ in formula X hereinabove and as one of the meanings for $Q_1$ and $Q_2$ in the definitions of the terms in formula I hereinbelow, is an alkoxy radical, preferably having from one to four carbon atoms, which can be arranged as straight or branched chains, including, for instance, but without limiting the generality of the foregoing, methoxy, ethoxy, n-propoxy, isopropoxy, n-butoxy, sec-butoxy, isobutoxy and tert-butoxy.

"Polyhalo-lower-alkoxy", as used herein, e.g., as one of the meanings for $Q_1$ in the definition of $Ac_3$ in formula I hereinabove and as one of the meanings for $Q_1$ and $Q_2$ in the definitions in formula I hereinbelow, is an alkoxy radical, preferably having from one to four carbon atoms and having from two to five halo substituents, i.e., fluoro, chloro, bromo and iodo, preferably fluoro and chloro, illustrated by dichloromethyl, difluoromethyl, dibromomethyl, diiodomethyl, trichloromethyl, trifluoromethyl, 2-chloro-1,1,2-trifluoroethyl, 2,2,2-trichloroethyl, 2,2,2-trifluoroethyl, 1,1,2,2,2-pentafluoroethyl, 1,1,2,2,-tetrafluoro-n-butyl, 2,2,3,3,3-pentafluoropropyl, and the like.

"Lower-alkanoyl", as used herein, e.g., as one of the meanings for $Ac_1$ in formula I hereinbelow, is an alkanoyl radical preferably having from two to four carbon atoms, illustrated by ethanoyl (acetyl), propanoyl (propionyl), n-butanoyl (butyryl), 2-methylpropanoyl, and the like.

The invention disclosed and claimed in said Ser. No. 462,388 resides in 3-R-3-($Ac_2NH$)-9-R'-9-($Ac_1NH$)-1,5-dioxaspiro[5.5]undecane where R and R' are each hydrogen or lower-alkyl, $Ac_1$ is lower-alkanoyl or 4-$Q_1$-benzoyl, and $Ac_2$ is 4-$Q_2$-benzoyl, where $Q_1$ and $Q_2$ each is lower-alkoxy or polyhalo-lower-alkoxy. This composition aspect of the invention is represented by the formula I

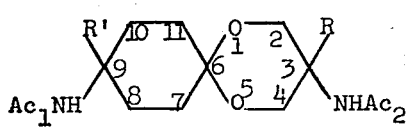

where R', R, Ac₁ and Ac₂ have the meanings designated above. The compounds of this composition aspect of the invention, when tested according to standard endocrinological evaluation procedures in animals, have been found to possess the applied use characteristics of having antifertility activity, e.g., in female rats, thereby indicating their utility as antifertility agents. Preferred embodiments are the compounds of formula I where R' is hydrogen and R is lower-alkyl; particularly preferred embodiments are the compounds of formula I where R' is hydrogen, R is methyl or ethyl, Ac₁ is acetyl, 4-trifluoromethyloxybenzoyl or 4-methoxybenzoyl and Ac₂ is 4-trifluoromethoxybenzoyl or 4-methoxybenzoyl.

The compounds of formula I where Ac₁ is the same as Ac₂ are prepared by reacting a 3-R-9-R'-1,5-dioxaspiro[5.5]-undecan-3,9-diamine of the formula II

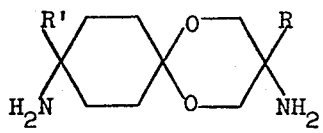

where R' and R have the meanings given hereinabove for formula I, with a 4-Q₂-benzoylating agent, preferably with at least two molar equivalents of a 4-Q₂-benzoyl halide of formula III

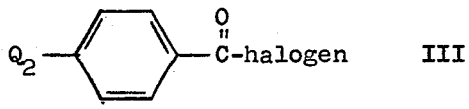

where Q₂ is defined as above in the definition of formula I. Other 4-Q₂-benzoylating agents are given hereinbelow.

The compounds of formula I where Ac₁ and Ac₂ are different are prepared by reacting an N-(3-amino-3-R-9-R'-1,5-dioxaspiro[5.5]undecan-9-yl)-acylamide of the formula IV where R', R and Ac₁ have the meanings given above for formula I, with a 4-Q₂-benzoylating agent, preferably with at least one molar equivalent of a 4-Q₂-benzoyl halide of formula III, as given hereinabove. Other 4-Q₂-benzoylating agents are noted hereinbelow.

The preparation of the intermediate 3-R-9-R'-1,5-dioxaspiro[5.5]undecan-3,5-diamine of formula II and the intermediate N-(3-amino-3-R-9-R'-1,5-dioxaspiro[5.5]undecan-9-yl)-acylamide of formula IV are prepared by the sequence of reactions illustrated structurally as follows:

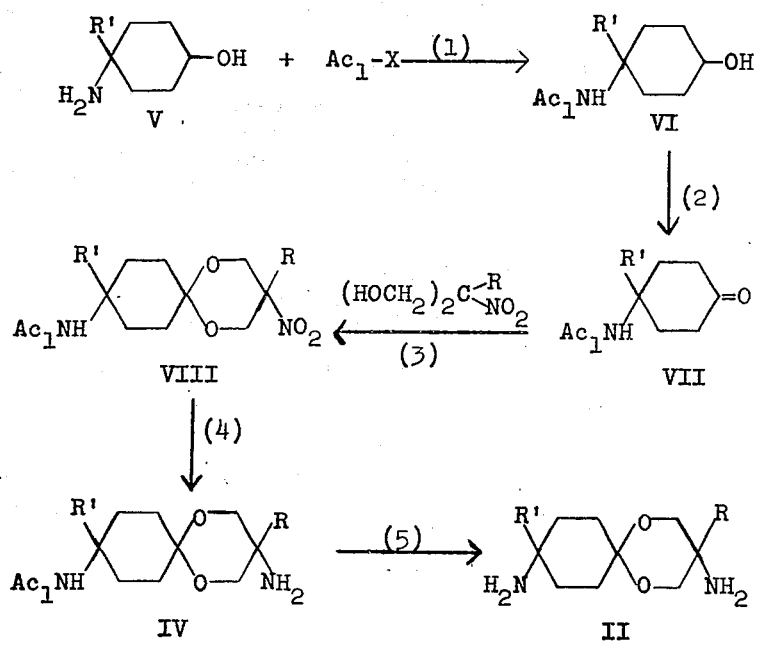

Thus, in step (1) the 4-amino-4-R'-cyclohexanol (V) is acylated, preferably with an acyl halide (Ac₁-X, where Ac₁ is defined above and X is halide, preferably chloride) or where Ac₁ is acetyl preferably with acetic anhydride to produce 4-Ac₁NH-4-R'-cyclohexanol (VI) which in step (2) is oxidized, e.g., with chromium trioxide, to give the corresponding 4-Ac₁NH-4-R'-cyclohexanone (VII). In step (3) said cyclohexanone (VII) is reacted with 2-R-2-nitro-1,3-propanediol to produce the 3-R-3-NO₂-9-Ac₁NH-9-R'-1,5-dioxaspiro[5.5]undecane (VIII) which is reduced, preferably by catalytic hydrogenation, to produce the N-(3-amino-3-R-9-R'-1,5-dioxaspiro[5.5]undecan-9-yl)-acylamide (IV), which, in turn, is hydrolyzed, preferably under aqueous alkaline conditions, to produce the 3-R-9-R'-1,5-dioxaspiro[5.5]-undecane-3,9-diamine (II). The initial starting materials (V) used in the above sequence of steps are known or are readily prepared from known compounds using generally known procedures which are illustrated hereinbelow. Similarly, the 2-NO₂-2-R-1,3-propanediols used in step (3) are known or are readily prepared from known compounds using generally known procedures.

Alternatively, the compound of formula VI where R' is hydrogen and Ac₁ is lower-alkanoyl is readily prepared by catalytic hydrogenation of the corresponding generally known 4-(Ac₁NH)phenol, as illustrated hereinbelow in the specific exemplary disclosure.

Preparation of the starting 4-amino-4-R'-cyclohexanol (V) where R' is lower-alkyl is conveniently carried out by the nucleophilic addition of a lower-alkanenitrile, preferably acetonitrile, to 4-R'-3-cyclohexenol in the presence of a strong acid and hydrolyzing the resulting 3.5-di-(lower-alkyl)-2-oxa-4-azabicyclo[3.2.2]-3-nonene in the form of its acid-addition salt, e.g., bisulfate if sulfuric acid is used as the strong acid. The intermediate 4-R'-3-cyclohexenols are generally known and are prepared stepwise by the known procedure of first reducing 4-R'-anisole with lithium and liquid ammonia in ether to produce 4-R'-1-methoxy-1,4-cyclohexadiene or methyl enol ether of 4-R'-3-cyclohexenone, next reacting said enol ether with a strong acid, e.g., aqueous oxalic acid, to produce 4-R'-3-cyclohexenone and reducing the latter with lithium aluminum hydride in ether to produce 4-R'-3-cyclohexenol.

The intermediates designated as II, IV only where Ac₁ is lower-alkanoyl and VIII only where Ac₁ is lower-alkanoyl are disclosed and claimed in copending U.S. patent application Ser. No. 462,389, filed Apr. 19, 1974.

The intermediates designated as VII, VIII and IV, each only where Ac₁ is 4-Q₁-benzoyl where Q₁ is lower-alkoxy or polyhalo-lower-alkoxy are aspects of the invention disclosed and claimed in said Ser. No. 462,388.

Thus, another composition aspect of Ser. No. 462,388 resides in 9-(Ac₃NH)-9-R'-3-R-3-Z-1,5-dioxaspiro[5.5]undecane of the formula IX

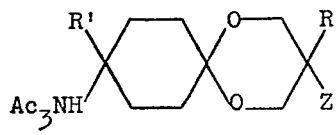

where R' and R are each hydrogen or lower-alkyl, Ac₃ is 4-Q₁-benzoyl, Q₁ is lower-alkoxy or polyhalo-lower-alkoxy, and Z is NO₂ or NH₂. Preferred embodiments of IX are the compounds where R40 is hydrogen, R is methyl or ethyl and Ac₃ is 4-methoxybenzoyl or 4-trifluoromethoxybenzoyl.

The compounds of formula IX are prepared by reacting 4-Ac₃NH-4-R'-cyclohexanone, where Ac₃ is 4-Q₁-benzoyl, Q₁ is lower-alkoxy or polyhalo-lower-alkoxy, and R' is hydrogen or lower-alkyl, with 2-R-2-nitro-1,3-propanediol, where R is hydrogen or lower-alkyl, to produce 3-nitro-3-R-9-(Ac₃NH)-9R'-1,5-dioxaspiro[5.5]undecane and reducing said 3-nitrospiroundecane to produce 3-amino-3-R-9-(Ac₃NH)-9-R'-1,5-dioxaspiro[5.5]undecane.

The nature of the starting materials, mode of synthesis, results of elementary analyses, examination of the final products of formula I and intermediates of formulas II, IV, VIII, IX and X by infrared nuclear magnetic resonance spectrographic analyses, all taken together, confirm the molecular structure assigned to these compounds.

The manner and process of making and using the invention will now be generally described so as to enable a person skilled in the art of medicinal chemistry to make and use the same, as follows:

The final products of formula I where Ac₁ is the same as Ac₂ are preferably prepared by reacting the approproiate diamine of formula II with at least two molar equivalents of the 4-Q₂-benzoyl halide of formula III in the presence of an acid-acceptor, that is, a basic substance capable of neutralizing the hydrogen halide formed by the reaction, for example, an alkali carbonate, preferably sodium carbonate or potassium carbonate, an alkali hydroxide, preferably sodium hydroxide or potassium hydroxide. The reaction was carried out preferably by carefully mixing the reactants with cooling (to about 0° to 10°C.) and stirring in a medium comprising water and a suitable water-immiscible organic solvent inert under the reaction conditions, e.g., ethylene dichloride, chloroform, methylene dichloride, benzene, ether, and the like; the reaction mixture preferably was then allowed to warm up to room temperature and to stand with stirring until the reaction was completed.

The final products of formula I where Ac₁ and Ac₂ are different are prepared by reacting an N-(3-amino-3-R-9-R'-1,5-dioxaspiro[5.5]undecan-9-yl)-acylamide of formula IV with a molar equivalent of the 4-Q₂-benzoyl halide of formula III using the above-described reaction conditions used for preparing the compounds of formula I where Ac₁ is the same as Ac₂.

Alternatively, other available 4-Q₂-benzoylating agents can be used in place of said 4-Q₂-benzoyl halides in the process aspects of the invention to prepare the compounds of formula I where Ac₁ is the same as and where it is different from Ac₂. For example, these 4-Q₂-benzoylations can be carried out by heating a lower-alkyl 4-Q₂-benzoate with a diamine of formula II or a monamine of formula IV or by reacting 4-Q₂-benzoic anhydride with said diamine or monamine. Also the products of formula I are obtained by heating said diamine or monamine with a 4-Q₂-benzoic acid either in the absence or presence of a suitable solvent, for example, dimethylformamide, tetrahydrofuran, benzene, ethylene dichloride, and the like, and either in the absence or presence of a dehydrating or an activating agent, e.g., dicyclohexylcarbodiimide, 1,1-carbonyldiimidazole and the like.

The reaction of 4-(Ac₁NH)-4-R'-cyclohexanone (VII) with 2-R-2-nitro-1,3-propanediol to produce 3-nitro-3-R-9-(Ac₁NH)-9-R'-1,5-dioxaspiro[5.5]undecane (VIII) is carried out by heating the reactants at about 50°–150°C., preferably about 70°–90°C. and preferably in the presence of an acid catalyst and preferably removing from the reaction mixture the water formed by the reaction. The reaction medium is preferably a water-immiscible, non-polar solvent inert to the reaction conditions, e.g., benzene, toluene, xylene, chloroform, carbon tetrachloride, and the like. The reaction is run preferably in refluxing benzene in the presence of p-toluenesulfonic acid as an acid catalyst and preferably having a continuous separator connected to the reaction vessel to collect the water formed by the reaction. The acid as catalyst can be any strong acid in catalytic amount, including strong inorganic acids, e.g., hydrochloric acid, hydrobromic acid, sulfuric acid, phosphoric acid, and the like, and organic sulfonic acid, e.g., p-toluenesulfonic, benzenesulfonic acid, methanesulfonic acid, ethanesulfonic acid, and the like. The reaction also can be run using a molar equivalent quantity of boron trifluoride etherate which acts both an acid catalyst and an agent capable of removing the water formed by the reaction.

The reaction of reducing 3-nitro-3-R-9-($Ac_1NH$)-9-R'-1,5-dioxaspiro[5.5]undecane (VIII) to produce 3-amino-3-R-9-($Ac_1NH$)-9-R'-1,5-dioxaspiro[5.5]undecane (IV) is carried out by reacting VIII with a reducing agent effective to reduce nitro to amino. The reduction is preferably run by catalytic hydrogenation in a solvent inert under the reaction conditions, e.g., ethanol, dimethylformamide, tetrahydrofuran, and the like, in the presence of a suitable hydrogenation catalyst, e.g., Raney nickel, platinum oxide, palladium-on-charcoal, other noble metal catalysts, and the like.

The hydrolysis of 3-amino-3-R-9-($Ac_1NH$)-9-R'-1,5-dioxaspiro[5.5]undecane (IV) to proruce 3-R-9-R'-1,5-dioxaspiro[5.5]undecan-3,9-diamine (II) is readily carried out by heating IV at about 50°–150°C., preferably about 90°–110°C., in aqueous alkali hydroxide solution, preferably aqueous sodium or potassium hydroxide solution. The hydrolysis also can be run using an alkali alkoxide in a lower-alkanol, e.g., sodium or potassium methoxide in methanol, sodium or potassium ethoxide in ethanol, sodium or potassium isobutoxide in isobutyl alcohol.

The reaction of 4-amino-4-R'-cyclohexanol (VI) with one molar equivalent of an acylating agent to produce 4-($Ac_1NH$)-4-R'-cyclohexanol (VI) is preferably carried out by reacting with an acyl halide ($Ac_1$-X) at about —5° to 10°C. in the presence of an acid-acceptor, e.g., an alkali carbonate or bicarbonate or hydroxide, by stirring the reactants in a reaction medium comprising water and a suitable water-immiscible organic solvent inert under the reaction conditions, e.g., ethylene dichloride, methylene dichloride, ether, benzene, and the like. Alternatively, where $Ac_1$ is lower-alkanoyl, other lower-alkanoylating agents, e.g., lower-alkanoic acid anhydride and lower-alkyl lower-alkanoate, can be used and non-aqueous media can be used, e.g., pyridine or other acid-acceptor solvents are conveniently used with a lower-alkanoyl halide, e.g., acetyl chloride, as the lower-alkanoylating agent; in fact, an non-aqueous medium such as pyridine is preferred when the highly reactive acetyl chloride is used. Another convenient method of preparing 4-($Ac_1NH$)-4-R'-cyclohexanol (VI) where R' is hydrogen and $Ac_1$ is lower-alkanoyl comprises the catalytic hydrogenation of the corresponding 4-($Ac_1NH$)phenol, as illustrated hereinbelow.

Preparation of the 4-amino-4-R'-cyclohexanol (V) where R' is lower-alkyl is carried out by carefully mixing 4-R'-cylcohex-3-enone with a chilled mixture of the alkanenitrile and strong acid, preferably concentrated sulfuric acid, preferably keeping the temperature of the reaction mixture between about —10°C. and +10°C. The reaction mixture, which contains the 3,5-di-(lower-alkyl)-2-oxa-4-azabicyclo[3.2.2] -3-nonene in the form of its acid-addition salt, e.g., bisulfate when sulfuric acid is used as the strong acid, is then allowed to warm up to room temperature. Hydrolysis of the said 2-oxa-4-azabicyclo[3.2.2]-3-nonene is achieved by adding water to the reaction mixture and heating it at about 75°–125°C., preferably between 90°–110°C., conveniently done on a steam bath.

The oxidation of 4-($Ac_1NH$)-4-R'-cyclohexanol (VI) to yield 4-($Ac_1NH$)-4-R'-cyclohexanone (VII or X) is generally carried out by reacting VI with an oxidizing agent capable of converting secondary alcohols to ketones. Preferred oxidizing agents are chromium trioxide in acetic or sulfuric acids or in pyridine, sodium or potassium dichromate and sulfuric acid, and the like. In preparing these intermediates (VI) stoichrometric quantities of chromium trioxide in aqueous sulfuric acid is used first mixing the reactants carefully while maintaining the reaction temperature at about 15°C. and then allowing for completion of the reaction at room temperature, i.e., about 25°C.

The best mode contemplated for carrying out the invention will now be set forth as follows:

A. 4-ACYLAMINOCYCLOHEXANOLS 1. 4-(4-METHOXYBENZAMIDO)CYCLOHEXANOL — A solution containing 34.56 g. of 4-aminocyclohexanol in 100 ml. of water was combined with a solution containing 42 g. of potassium carbonate in 100 ml. of water and the resulting solution was cooled to about 10°C. using an ice-water bath. To the cooled solution was added dropwise with stirring over a period of one hour a solution containing 51.2 g. of 4-methoxybenzoyl chloride in 25 ml. of ethylene dichloride, whereupon a voluminous white precipitate separated. The resulting mixture was stirred at room temperature for one hour and then allowed to stand overnight (about 15 hours) at room temperature. The precipitate was collected, washed well with water, dried at 60°C. under reduced pressure (one-third atmosphere), recrystalized from boiling methanol and dried at 50°C. for eighteen hours at one-third atmosphere to yield 21.9 g. of 4-(4-methoxybenzamido)cyclohexanol, m.p. 218°–219°C.

2. 4-(4-TRIFLUOROMETHOXYBENZAMIDO)-CYCLOHEXANOL — 3.8 g., m.p. 245°–246.5°C., was obtained following the procedure described in Example A-1 using a mixture of 3.6 g. of 4-aminocyclohexanol, 4.82 g. of potassium carbonate, 50 ml. of water and 50 ml. of ethylene dichloride, 6.72 g. of 4-trifluoromethoxybenzyl chloride in 25 ml. of ethylene dichloride and recrystallization from benzene-methanol.

3. 4-METHYL-4-(4-TRIFLUOROMETHOXYBENZAMIDO)CYCLOHEXANOL — To a solution cooled to 5°C. and containing 22.4 g. of 4-amino-4-methylcyclohexanol in 100 ml. of 2N potassium hydroxide solution and 150 ml. of water was added dropwise with vigorous stirring over a period of two hours 39 g. of 4-trifluoromethoxybenzoyl chloride whereupon a white gummy solid separated. The resulting mixture was stirred at room temperature for six hours and then allowed to stand overnight at room temperature. The reaction mixture was extracted with methylene dichloride, the extract dried over anhydrous potassium carbonate and the solvent distilled off in vacuo to yield, as a clear viscous oil, 44.5 g. of 4-methyl-4-(4-trifluoromethoxybenzamido)cyclohexanol.

The above intermediate 4-amino-4-methylcyclohexanol was prepared as follows: To 40 ml. of chilled concentrated sulfuric acid was added dropwise with stirring 20 ml. of acetonitrile at such a rate to maintain the temperature between −5° and +5°C. To the resulting solution kept below 10°C. was added dropwise with stirring over a period of about forty-five minutes a solution containing 11.3 g. of 4-methyl-3-cyclohexenol in 10 ml. of acetonitrile. The clear brown solution was allowed to stand at 5°C. over the weekend (about 65 hours) and then poured onto 500 g of ice. The resulting solution, which contains 3,5-dimethyl-2-oxa-4-azabicyclo[3.2.2]-3-nonene as its bisulfate acid-addition salt, was stirred on a steam bath for seven hours, the hot mixture was treated with decolorizing charcoal and filtered; and, the resulting filtrate was treated with a solution of 50 g. of sodium hydroxide in 75 ml. of water. The resulting solution was concentrated in vacuo to one-half volume, made strongly basic with 35% aqueous sodium hydroxide solution and the alkaline solution extracted with methylene dichloride (4 × 75 ml.). The combined extracts were dried over anhydrous potassium carbonate and the solvent distilled off in vacuo to yield, as a clear, very viscous oil, 6.25 g. of 4-amino-4-methylcyclohexanol.

Following the procedure described in the immediately preceding paragraph but using a molar equivalent quantity of 4-ethyl-3-cyclohexenol in place of 4-methyl-3-cyclohexenol, there is obtained 4-amino-4-ethylcyclohexanol via the intermediate 5-ethyl-3-methyl-2-oxa-4-azabicyclo[3.2.2]-3-nonane as its bisulfate salt.

In the foregoing preparations of 4-amino-4-(loweralkyl-cyclohexanols the intermediate 3,5-di-(loweralkyl)-2-oxa-4-azabicyclo[3.2.2]-3-nonane and acid-addition salt can be isolated before conversion by hydrolysis to said 4-amino-4-(lower-alkyl)-cyclohexanol, as illustrated as follows: To a stirred and chilled (to −20°C. using a solid carbon dioxide-isopropyl alcohol bath) of 80 ml. of concentrated sulfuric acid was added dropwise 40 ml. of acetonitrile at such a rate that the reaction temperature did not exceed +5°C. To the resulting chilled solution was added dropwise with stirring and cooling a solution of 27.4 g. of 4-methyl-3-cyclohexenol in 20 ml. of acetonitrile, keeping the reaction temperature below +5°C. The resulting reaction solution was kept at 0°C. for 45 minutes and then allowed to warm up to room temperature (about 25°C.) and stand for about sixteen hours (overnight). The reaction solution was slowly poured into a solution of 120 g. of sodium hydroxide in 600 ml. of ice water over a period of sixty minutes. The precipitated sodium sulfate was filtered off and the filtrate was extracted with chloroform (5 × 75 ml.). The extract was dried over anhydrous magnesium sulfate, the solvent removed by distillation under reduced pressure and the residual oil fractionally distilled under reduced pressure to yield, as a clear colorless oil, 17.5 g. of 3,5-dimethyl-2-oxa-4-azabicyclo[3.2.2]-3-nonane in free base form, b.p. 73°–74.5°C. at 13 mm., $n^{27}=1.4753$, which was converted into its hydrochloride as follows: said free base was dissolved in 300 ml. of dry ether and the solution treated with ethereal hydrogen chloride until the mixture was strongly acid. The resulting white precipitate (20.8 g.; m.p. 124°–128°C.) was collected, washed with dry ether, dried in vacuo at 40°C., recrystallized from acetonitrile and a little ether, and dried in vacuo at 50°C. to yield 3,5-dimethyl-2-oxa-4-azabicyclo[3.2.2]-3-nonane hydrochloride, m.p. 140°–142°C. When this hydrochloride salt in aqueous solution is heated on a steam bath by the procedure described above for conversion of the solution of the corresponding bisulfate salt from the 2-oxa-4-azabicyclo[3.2.2]-3-nonane to the monocyclic 4-aminocyclohexanol, there is obtained 4-amino-4-methycyclohexanol.

4. 4-ACETAMIDOCYCLOHEXANOL — A solution of 64.0 g. of 4-acetamidophenol in 400 ml. of 95% ethanol also containing 1.0 g. of 5% rhodium-on-alumina was hydrogenated at 95°–133°C. for four hours at a starting hydrogen pressure of 1850 p.s.i. Since only 34% of the theoretical quantity of hydrogen had been taken up, an additional 3.0 g. of 5% rhodium-on-alumina was added and hydrogenation was continued at 90°–110°C. for eight hours starting with 1850 p.s.i. of hydrogen, the total combined uptake of hydrogen being 90%. The catalyst was filtered off and the solvent was distilled off in vacuo to yield, as a white solid, 70.5 g. of 4-acetamidocyclohexanol. A small portion of this compound melted at 160°–162.5°C. after recrystallization from acetone.

5. 4-ACETAMIDO-4-METHYLCYCLOHEXANOL — A mixture containing 12.9 g. of 4-amino-4-methylcyclohexanol, 10.2 g. of acetic anhydride, 1.7 g. of sodium acetate and 15 ml. of glacial acetic acid is refluxed with stirring for 90 minutes, cooled to room temperature, 10 ml. of water added and chilled. The resulting precipitate is collected, washed with cold water and dried in vacuo at 60°C. to yield 4-acetamido-4-methylcyclohexanol.

Following the procedures described in Example A-4 or A-5 but using molar equivalent quantities of the appropriate reactants, the compounds of Examples A-6 through A-10 are produced.

6. 4-METHYL-4-PROPIONAMIDOCYCLOHEXANOL using 4-amino-4-methylcyclohexanol and propionic anhydride as in Example A-5.

7. 4-ACETAMIDO-4-ETHYCYCLOHEXANOL using 4-amino-4-ethylcyclohexanol and acetic anhydride as in Example A-5.

8. 4-PROPIONAMIDOCYCLOHEXANOL using 4-propionamidophenol as in Example A-4.

9. 4-BUTYRAMIDOCYCLOHEXANOL using 4-butyramidophenol as in Example A-4.

10. 4-ISOBUTYRAMIDOCYCLOHEXANOL using 4-isobutyramidophenol as in Example A-4.

11. 4-(4-DIFLUOROMETHOXYBENZAMIDO)-CYCLOHEXANOL is prepared following the procedure described in Example A-1 using corresponding molar equivalent quantities of 4-aminocyclohexanol and 4-difluoromethoxybenzoyl chloride.

B. 4-ACYLAMINOCYCLOHEXANONES 1. 4-ACETAMIDOCYCLOHEXANONE — To a stirred solution cooled to 10°C. and containing 471 g. of 4-acetamidocyclohexanol, 3 liters of acetone and 450 ml. of water was slowly added a solution containing 210 g. of chromium trioxide in 900 ml. of water and 183 ml. of concentrated sulfuric acid, the addition being at such a rate as to keep the reaction temperature at about 15°C. The reaction mixture was then stirred at room temperature for several hours and then allowed to stand at room temperature overnight (about 15 hours). The liquid was decanted from the semi-solid blue green salts and most of the solvent was removed at reduced pressure. The residue was combined with saturated salts; 300 ml. of water was added; and, the mixture was neutralized with solid sodium carbonate. The mixture was shaked well with warm chloroform, filtered and the layers separated. The chloroform layer was heated in vacuo to remove the solvent and the remaining white solid was recrystallized from dry acetone to yield 284 g. of 4-acetamidocyclohexanone, m.p. 133°–136°C.

2. 4-(4-TRIFLUOROMETHOXYBENZAMIDO)-CYCLOHEXANONE, 17.0 g., m.p. 166°–167°C., was prepared following the procedure described in Example B-1 using 21.2 g. of 4-(4-trifluoromethoxybenzamido)cyclohexanol, 350 ml. of acetone, 5.0 g. of chromium trioxide, 18 ml. of water, 4.2 ml. of concentrated sulfuric acid and recrystallization from chloroform-cyclohexane.

3. 4-(4-METHOXYBENZAMIDO)CYCLOHEXANONE — To a stirred mixture containing 24.9 g. of 4-(4-methoxybenzamido)cyclohexanol, 200 ml. of acetone and 300 ml. of chloroform was added dropwise over a period of 45 minutes a solution containing 5.6 g. of chromium trioxide, 16 ml. of water and 5 ml. of concentrated sulfuric acid, whereupon the reaction temperature rose from about 20° to about 35°C. The mixture of pale yellow solution and blue-green salts was stirred at 25°C. for one hour, filtered and the filtrate diluted with an equal volume of water. The layers were separated and the aqueous layer was extracted with chloroform. The organic layers were combined, washed with saturated brine solution, dried over anhydrous potassium carbonate and the solvent distilled off under reduced pressure to yield, as a white solid, 11.6 g. of 4-(4-methoxybenzamido)cyclohexanone. When recrystallized from acetone-cyclohexane, this compound was found to melt at 190°–191°C.

4. 4-METHYL-4-(4-TRIFLUOROMETHOXYBENZAMIDO)CYCLOHEXANONE, 35.2 g. as a clear, pale yellow, very viscous oil, was prepared following the procedure described in Example B-2 using 40.2 g. of 4-methyl-4-(4-trifluoromethoxybenzamido)cyclohexanol dissolved in 300 ml. of acetone, 33 ml. of a solution containing 9.0 g. of chromium trioxide, 7.8 ml. of concentrated sulfuric acid and water, and using methylene dichloride to extract the product from the reaction mixture.

Following the procedure described in Example B-1 but using a molar equivalent quantity of the appropriate 4-acylamido-4-R'-cyclohexanol, the compounds of Examples B-5 through B-10 are produced.

5. 4-ACETAMIDO-4-METHYLCYCLOHEXANONE from 4-acetamido-4-methylcyclohexanol.

6. 4-ACETAMIDO-4-ETHYLCYCLOHEXANONE from 4-acetamido-4-ethylcyclohexanol.

7. 4-PROPIONAMIDOCYCLOHEXANONE from 4-propionamidocyclohexanol.

8. 4-BUTYRAMIDOCYCLOHEXANONE from 4-butyramidocyclohexanol.

9. 4-ISOBUTYRAMIDOCYCLOHEXANONE from 4-isobutyramidocyclohexanol.

10. 4-(4-DIFLUOROMETHOXYBENZAMIDO)-CYCLOHEXANONE from 4-(4-difluoromethoxybenzamido)cyclohexanol.

C.
9-ACYLAMIDO-3-NITRO-1,5-DIOXASPIRO[5.5]UNDECANES

1. N-(3-METHYL-3-NITRO-1,5-DIOXASPIRO[5.5]UNDECAN-9-YL)ACETAMIDE — A stirred mixture containing 9.3 g. of 4-acetamidocyclohexanone, 8.12 g. of 2-methyl-2-nitro-1,3-propanediol, 0.05 g. of p-toluenesulfonic acid monohydrate and 150 ml. of benzene was boiled under reflux for twenty hours with a continuous separator connected to the reaction vessel to collect the water formed by the reaction. The reaction mixture was shaken well with 50 ml. of 5% aqueous sodium bicarbonate solution; the phases were separated and the aqueous phase was extracted with chloroform; the benzene phase and chloroform extract were combined and dried over anhydrous potassium carbonate; and, the benzene and chloroform were distilled off in vacuo to leave 16.4 g. of crystalline solid which was recrystallized from chloroform-benzene and dried for eighteen hours at 50°C. and one-thrid atmosphere to yield 11.1 g. of N-(3-methyl-3-nitro-1,5-dioxaspiro[5.5]undecan-9-yl)acetamide, m.p. 158°–159°C.

2. N-(3-NITRO-1,5-DIOXASPIRO[5.5]UNDECAN-9-YL)ACETAMIDE — A mixture of 26.4 g. of 4-acetamidocyclohexanone and 19.3 g. of 2-nitro-1,3-propanediol was dissolved in 100 ml. of acetonitrile with slight warming. To this solution was added 22.7 g. of boron trifluoride etherate and the resulting solution was heated on a steam bath for fifteen minutes allowing the ether to distill off, whereupon the reaction temperature increased to about 80°C. Most of the solvent was distilled off under reduced pressure and the residue was poured, with stirring, into a mixture containing 14 g. of potassium carbonate in 220 ml. of ice and water. The mixture was extracted with chloroform; the chloroform extract was dried over anhydrous potassium carbonate; and the chloroform was distilled off in vacuo to yield a very viscous oil which crystallized at room temperature. The crystalline product was recrystallized from 300 ml. of acetone to yield 12.81 g. of N-(3-nitro-1,5-dioxaspiro[5.5]undecan-9-yl)acetamide, m.p. 170°–172°C. A small sample was recrystallized from methanol and was found to melt at 177°–178°C.

3. N-(3-ETHYL-3-NITRO-1,5-DIOXASPIRO[5.5]UNDECAN-9-YL)ACETAMIDE, 31.8 g. as a clear, very viscous oil, was obtained following the procedure described in Example C-1 using 15.5 g. of 4-acetamidocyclohexanone, 16.4 g. of 2-ethyl-2-nitro-1,3-propanediol, 0.5 g. of p-toluenesulfonic acid monohydrate, and 150 ml. of benzene.

4. N-(3-METHYL-3-NITRO-1,5-DIOXASPIRO[5.5]UNDECAN-9-YL)-4-METHOXYBENZAMIDE — 16.9 g., m.p. 191°–192°C., was prepared following the procedure described in Example C-1 using 17.2 g. of 4-(4-methoxybenzamido)cyclohexanone, 9.45 g. of 2-methyl-2-nitro-1,3-propanediol, 0.2 g. of p-toluenesulfonic acid monohydrate, 500 ml. of benzene and recrystallization from 95% ethanol (150 ml.).

5. N-(3,9-DIMETHYL-3-NITRO-1,5-DIOXASPIRO[5.5]UNDECAN-9-YL)-4-TRIFLUOROMETHOXYBENZAMIDE, 8.2 g., m.p. 228°–229°C., was prepared following the procedure described in Example C-1 using 17.6 g. of 4-methyl-4-(4-trifluoromethoxybenzamido)cyclohexanone, 10.8 g. of 2-methyl-2-nitro-1,3-propanediol, 0.5 g. of p-toluenesulfonic acid monohydrate, 200 ml. of benzene, a refluxing time of seven hours and recrystallization from acetone.

Following the procedure described in Example C-1 but using molar equivalent quantities of the appropriate 4-acylamido-4-R'-cyclohexanone and 2-nitro-2-R-1,3-propanediol, respectively, the compounds of Examples C-6 through C-13 are produced.

6. N-(3-METHYL-3-NITRO-1,5-DIOXASPIRO[5.5]UNDECAN-9-YL)PROPIONAMIDE using 4-propionamidocyclohexanone and 2-methyl-2-nitro-1,3-propanediol.

7. N-(3-METHYL-3-NITRO-1,5-DIOXASPIRO[5.5]UNDECAN-9-YL)BUTYRAMIDE using 4- butyramidocyclohexanone and 2-methyl-2-nitro-1,3-propanediol.

8. N-(3-METHYL-3-NITRO-1,5-DIOXASPIRO[5.5]UNDECAN-9-YL)ISOBUTYRAMIDE using 4-isobutyramidocyclohexanone and 2-methyl-2-nitro-1,3-propanediol.

9. N-(3,9-DIMETHYL-3-NITRO-1,5-DIOXASPIRO[5.5]UNDECAN-9-YL)ACETAMIDE using 4-acetamido-4-methylcyclohexane and 2-methyl-2-nitro-1,3-propanediol.

10. N-(3,9-DIETHYL-3-NITRO-1,5-DIOXASPIRO[5.5]UNDECAN-9-YL)ACETAMIDE using 4-acetamido-4-ethylcyclohexanone and 2-ethyl-2-nitro-1,3-propanediol.

11. N-(9-METHYL-3-NITRO-1,5-DIOXASPIRO[5.5]UNDECAN-9-YL)ACETAMIDE using 4-acetamido-4-methylcyclohexanone and 2-nitro-1,3-propanediol.

12. N-(3-METHYL-3-NITRO-1,5-DIOXASPIRO[5.5]UNDECAN-9-YL)-4-DIFLUOROMETHOXYBENZAMIDE using 4-(4-difluoromethoxybenzamido)cyclohexanone and 2-methyl-2-nitro-1,3-propanediol.

13. N-(3-METHYL-3-NITRO-1,5-DIOXASPIRO[5.5]UNDECAN-9-YL)-4-TRIFLUOROMETHOXYBENZAMIDE using 4-(4-trifluoromethoxybenzamido)cyclohexanone and 2-methyl-2-nitro-1,3-propanediol.

D.
9-ACYLAMIDO-3-AMINO-1,5-DIOXASPIRO[5.5]UNDECANES

1. N-(3-AMINO-3-METHYL-1,5-DIOXASPIRO[5.5]UNDECAN-9-YL)ACETAMIDE — A mixture containing 200 g. of N-(3-methyl-3-nitro-1,5-dioxaspiro[5.5]undecan-9-yl)acetamide, 10 g. of Raney nickel and sufficient 95% ethanol to produce a total volume of 17 ml. was treated under catalytic hydrogenation conditions at 50°–60°C. for five hours stirring with an initial hydrogen pressure of 900 psi and ending with the hydrogen pressure of 650 psi. The reaction mixture was filtered and the filtrate heated on a steam bath in vacuo to remove the solvent, thereby yielding, as a clear viscous oil, 185 g. of N-(3-amino-3-methyl-1,5-dioxaspiro[5.5]undecan-9-yl)acetamide.

2. N-(3-AMINO-1,5-DIOXASPIRO[5.5]UNDECAN-9-YL)ACETAMIDE, 12.1 g. as a viscous oil, was prepared following the procedure described in Example D-1 using 12.8 g. of N-(3-nitro-1,5-dioxaspiro[5.5]undecan-9-yl)acetamide, 300 ml. of tetrahydrofuran as the solvent, 1 teaspoonful of Raney nickel, a reaction temperature of 40°–50°C. and initial hydrogen pressure of 980 psi and a final hydrogen pressure of 950 psi.

3. N-(3-AMINO-3-ETHYL-1,5-DIOXASPIRO[5.5]UNDECAN-9-YL)ACETAMIDE, 25.5 g. as a clear viscous oil, was prepared following the procedure described in Example D-1 using 28.6 g. of N-(3-ethyl-3-nitro-1,5-dioxaspiro[5.5]undecan-9-yl)acetamide, 300 ml. of 95% ethanol, 3 teaspoonsful of Raney nickel, reaction temperature of 25°–27°C. and initial hydrogen pressure of 1,000 psi and a final hydrogen pressure of 900 psi.

4. N-(3-AMINO-3-METHYL-1,5-DIOXASPIRO[5.5]UNDECAN-9-YL)-4-METHOXYBENZAMIDE, 9.21 g. as a clear, colorless, glassy material which slowly crystallized at room temperature, was prepared following the procedure described in Example D-1 using 9.3 g. of N-(3-methyl-3-nitro-1,5-dioxaspiro[5.5]undecan-9-yl)-4-methoxybenzamide, a mixture of 80 ml. of ethanol and 10 ml. of dimethylformamide and a solvent, one-half of a teaspoonful of Raney nickel, a reaction temperature of 45°–50°C. for two hours and initial hydrogen pressure of 970 psi and a final hydrogen pressure of 750 psi.

5. N-(3-AMINO-3,9-DIMETHYL-1,5-DIOXASPIRO[5.5]UNDECAN-9-YL)TRIFLUOROMETHOXYBENZAMIDE, 8.6 g. as a white crystal solid, was prepared following the procedure described in Example D-1 using 9.5 g. of N-(3,9-dimethyl-3-nitro-1,5-dioxaspiro[5.5]undecan-9-yl)-4-trifluoromethoxybenzamide, 140 ml. of dimethylformamide, one-half teaspoonful of Raney nickel, a reaction temperature at about 50°–60°C. for five hours, an initial hydrogen pressure of 1,000 psi and a final hydrogen pressure of 860 psi.

Following the procedure described in Example D-1 but using a molar equivalent quantity of the appropriate N-(3-R-3-nitro-9-R'-1,5-dioxaspiro[5.5]undecan-9-yl)acylamide, the compounds of Examples D-6 through D-13 are produced.

6. N-(3-AMINO-3-METHYL-1,5-DIOXASPIRO[5.5]UNDECAN-9-YL)PROPIONAMIDE from N-(3-methyl-3-nitro-1,5-dioxaspiro[5.5]undecan-9-yl)propionamide.

7. N-(3-AMINO-3-METHYL-1,5-DIOXASPIRO[5.5]UNDECAN-9-YL)BUTYRAMIDE from N-(3-methyl-3-nitro-1,5-dioxaspiro[5.5]-undecan-9-yl)butyramide.

8. N-(3-AMINO-3-METHYL-1,5-DIOXASPIRO[5.5]UNDECAN-9-YL)ISOBUTYRAMIDE from N-(3-methyl-3-nitro-1,5-dioxaspiro[5.5]undecan-9-yl)isobutyramide.

9. N-(3-AMINO-3,9-DIMETHYL-1,5-DIOXASPIRIO[5.5]UNDECAN-9-YL)ACETAMIDE from N-(3,9-dimethyl-3-nitro-1,5-dioxaspiro[5.5]undecan-9-yl)acetamide.

10. N-(3-AMINO-3,9-DIETHYL-1,5-DIOXASPIRO[5.5]UNDECAN-9-YL)ACETAMIDE from N-(3,5-diethyl-3-nitro-1,5-dioxaspiro[5.5]undecan-9-yl)acetamide.

11. N-(3-AMINO-9-METHYL-1,5-DIXOASPRIO[5.5]UNDECAN-9-YL)ACETAMIDE from N-(9-methyl-3-nitro-1,5-dioxaspiro[5.5]undecan-9-yl)acetamide.

12. N-(3-AMINO-3-METHYL-1,5-DIOXASPIRO[5.5]UNDECAN-9-YL)-4-DIFLUOROMETHOXYBENZAMIDE from N-(3-methyl-3-nitro-1,5-dioxaspiro[5.5]undecan-9-yl)-4-difluoromethoxybenzamide.

13. N-(3-AMINO-3-METHYL-1,5-DIOXASPIRO[5.5]UNDECAN-9-YL)-4-TRIFLUOROMETHOXYBENZAMIDE from N-(3-methyl -3-nitro-1,5-dioxaspiro[5.5]undecan-9-yl)-4-trifluoromethoxybenzamide.

E. 1,5-DIOXASPIRO[5.5]UNDECAN-3,9-DIAMINE 1. 3-METHYL-1,5-DIOXASPIRO[5.5]UNDECAN-3,9-DIAMINE — A 370 g. portion of N-(3-amino-3-methyl-1,5-dioxaspiro[5.5]undecan-9-yl) acetamide was dissolved in a solution containing 134 g. of potassium hydroxide in 1800 ml. of water and the resulting reaction mixture was refluxed with stirring for two hours. The mixture was allowed to cool to about 50°C. and was then concentrated in vacuo by heating on a steam bath until a semi-solid residue appeared. To the mixture was added two liters of ethyl acetate and the resulting warm mixture was stirred for several minutes, filtered and the filter-cake washed with warm ethyl acetate. The layers of the filtrate were separted and the ethyl acetate layer was dried over anhydrous potassium carbonate. The dried solution was concentrated in vacuo to remove the ethyl acetate thereby leaving, as a clear, amber oil, 300 g. of 3-methyl-1,5-dioxaspiro[5.-5]undecan-3,9-diamine. A 240 g. portion of this diamine was dissolved in isopropyl alcohol and to the solution was added a slight excess of concentrated hydrochloric acid whereupon the dihydrochloride salt separated. After the mixture had been cooled, the precipitate was collected and washed successively with dry ether and absolute ethanol to yield 152 g. of 3-methyl-1,5-dioxaspiro[5.5]undecan-3,9-diamine dihydrochloride, m.p. 258°–260°C.

2. 1,5-DIOXASPIRO[5.5]UNDECAN-3,9-DIAMINE, 5.6 g. as a clear, colorless, viscous oil, b.p. 108°–120°C. at 0.02 mm., was prepared following the procedure described in Example E-1 using 12.0 g. of N-(3-amino-1,5-dioxaspiro[5.5]undecan-9-yl)-acetamide, a solution of 8.0 g. of potassium hydroxide in 50 ml. of water, a reflux period of three hours, chloroform as the extracting solvent and fractional distillation under reduced pressure of the oil remaining after removal of the chloroform.

3. 3-ETHYL-1,5-DIOXASPIRO[5.5]UNDECAN-3,9-DIAMINE,8.25 g. as a clear, colorless, viscous oil, b.p. 110°–113°C. at 0.05 mm, was obtained as in Example E-1 using 20.6 g. of N-(3-amino-3-ethyl-1,5-dioxaspiro[5.5]undecan-9-yl)-acetamide, 10 g. of potassium hydroxide in 100 ml. of water, a refluxing period of five and one-half hours, ethyl acetate as the extracting solvent and purification of the product by fractional distillation under reduced pressure.

Following the procedure described in Example E-1 but using in place of N-(3-amino-3-methyl-1,5-dioxaspiro[5.5]undecan -9-yl)acetamide a molar equivalent quantity of the appropriate N-(3-amino-3-R-9-R'-1,5-dioxaspiro-[5.5]undecan-9-yl)acylamide, the compounds of Examples E-4 through E-9 are produced.

4. 3-METHYL-1,5-DIOXASPIRO[5.5]UNDECAN-3,9-DIAMINE from N-(3-amino-3-methyl-1,5-dioxaspiro[5.5]undecan-9-yl)-propionamide.

5. 3-METHYL-1,5-DIOXASPIRO[5.5]UNDECAN-3,9-DIAMINE from N-(3-amino-3-methyl-1,5-dioxaspiro[5.5]undecan-9-yl)-butyramide.

6. 3-METHYL-1,5-DIOXASPIRO[5.5UNDECAN-3,9-DIAMINE from N-(3-amino-3-methyl-1,5-dioxaspiro[5.5]undecan-9-yl)isobutyramide.

7. 3,9-DIMETHYL-1,5-DIOXASPIRO[5.5]UNDECAN-3,9-DIAMINE from N-(3-amino-3,9-dimethyl-1,5-dioxaspiro[5.5]undecan-9-yl)acetamide.

8. 3,9-DIETHYL-1,5-DIOXASPIRO[5.5]UNDECAN-3,9-DIAMINE from N-(3-amino-3,9-diethyl-1,5-dioxaspiro[5.5]undecan-9-yl)acetamide.

9. 9-METHYL-1,5-DIOXASPIRO[5.5]UNDECAN-3,9-DIAMINE from N-(3-amino-9-methyl-1,5-dioxaspiro[5.5]undecan-9-yl)-acetamide.

F. 3,9-DI-(ACYLAMIDO)-1,5-DIOXASPIRO[5.-5]UNDECANES

1. N,N'-(3-METHYL-1,5-DIOXASPIRO[5.5]UNDECANE-3,9-DIYL)BIS(4-TRIFLUOROMETHOXYBENZAMIDE) — To a stirred mixture containing 8.0 g. of 3-methyl-1,5-dioxaspiro[5.5]undecan-3,9-diamine in 50 ml. of dry ethylene dichloride, 50 ml. of 10% aqueous potassium carbonate solution and 25 ml. of water, chilled to 10°C. in an ice bath was added dropwise with stirring over a period of one hour a solution containing 19.3 g. of 4-trifluoromethoxybenzoyl chloride in 50 ml. of dry ethylene dichloride. The mixture was stirred while warming to room temperature and then for an additional two hours at room temperature. After the mixture had been stirred overnight at 5°C., it was shaken well with 100 ml. of chloroform and the layers separated. The chloroform layer was dried over anhydrous potassium carbonate and the chloroform distilled off under reduced pressure. The remaining white solid was recrystallized from ethylene dichloride-n-hexane to yield 15.14 g. of N,N'-(3-methyl-1,5-dioxaspiro[5.5]undecane-3,9-diyl)bis(4-trifluoromethoxybenzamide, m.p. 202.5°–203.5°C. Evaporation of the mother layer to dryness under reduced pressure gave 7.4 g. of white solid which was recrystallized, using decolorizing charcoal, from ethylene dichloride-n-hexane to yield another 6.3 g. of the product, m.p. 201°–203°C.

2. N,N'-(3-METHYL-1,5-DIOXASPIRO[5.-5]UNDECAN-3,9-DIYL)BIS(4-METHOXYBENZAMIDE), 6.1 g., m.p. 203°–204°C., was prepared following the procedure described in Example F-1 using 4.46 g. of 3-methyl-1,5-dioxaspiro[5.5]undecan-3,9-diamine in 50 ml. of ethylene dichloride, 7.0 g. of potassium carbonate in 70 ml. of water, 8.55 g. of 4-methoxybenzoyl chloride in 50 ml. of ethylene dichloride, and recrystallization from absolute ethanol using decolorizing charcoal.

3. N,N'-(3-METHYL-1,5-DIOXASPIRO[5.-5]UNDECAN-3,9-DIYL)BIS(4-DIFLUOROMETHOXYBENZAMIDE), 21.1 g., m.p. 200°–201°C., was prepared following the procedure described in Example F-1 using 13.6 g. of 3-methyl-1,5-dioxaspiro[5.5]undecan-3,9-diamine dihydrochloride in 100 ml. of water, 27.6 g. of potassium carbonate in 100 ml. of ethylene dichloride and 20.7 g. of 4-difluoromethoxybenzoyl chloride in 50 ml. of ethylene dichloride; isolating the solid product from the reaction mixture by filtration; and, recrystallizing it from isopropyl alcohol.

4. N,N'-(3-ETHYL-1,5-DIOXASPIRO[5.5]UNDECAN-3,9-DIYL)BIS(4-TRIFLUOROMETHYBENZAMIDE), 18.9 g., m.p. 184.5°–185.5°C., was prepared following the procedure described in Example F-1 using 8.25 g. of 3-ethyl-1,5dioxaspiro5.5]undecan-3,9-diamine in 100 ml. of ethylene dichloride, 13.8 g. of potassium carbonate in 80 ml. of water, 17.2 g. of 4-trifluoromethoxybenzoyl chloride in 40 ml. of ethylene dichloride, and recrystallization from chloroform.

5. N,N'-(1,5-DIOXASPIRO[5.5]UNDECAN-3,9-DIYL)BIS-(4-TRIFLUOROMETHOXYBENZAMIDE), 11.4 g., m.p. 260°–261°C., was prepared following the procedure described in Example F-1 using 5.6 g. of 1,5-dioxaspiro[5.5]undecan-3,9 -diamine in 50 ml. of ethylene dichloride, 8.3 g. of potassium carbonate in 100 ml. of water, 13.5 g. of 4-trifluoromethoxybenzoyl chloride in 50 ml. of ethylene dichloride, and recrystallization from carbon tetrachloride-methanol.

6. N-(9-ACETAMIDO-3-METHYL-1,5-DIOXASPIRO[5.5]UNDECAN-3-YL)-4-TRIFLUOROMETHOXYBENZAMIDE, 8.26 g., m.p. 197°–198°C., was prepared following the procedure described in Example F-1 using 7.8 g. of N-(3-amino-3-methyl-1,5-dioxaspiro[5.5]undecan-9-yl)acetamide in 50 ml. of ethylene dichloride, 5.5 g. of potassium carbonate in 60 ml. of water, 8.3 g. of 4-trifluoromethoxybenzoyl fluoride in 50 ml. of ethylene dichloride, and recrystallization from carbon tetrachloride-methanol.

7. N,N'-(3,9-DIMETHYL-1,5-DIOXASPIRO[5.5]UNDECAN-3,9-DIYL)BIS(4-TRIFLUOROMETHOXYBENZAMIDE), 5.4 g., amorphous white powder, was prepared following the procedure described in Example F-1 using 4.5 g. of 3,9-dimethyl-1,5-dioxaspiro[5.5]undecan-3,9-diamine in 50 ml. of ethylene dichloride, 2.1 g. of potassium carbonate in 50 ml. of water, and 2.5 g. of 4-trifluoromethoxybenzoyl chloride in 20 ml. of ethylene dichloride.

8. N-(9-ACETAMIDO-3-ETHYL-1,5-DIOXASPIRO[5.5]UNDECAN-3-YL)-4-TRIFLUOROMETHOXYBENZAMIDE, 5.7 g., m.p. 198°–199°C., was prepared following the procedure described in Example F-1 using 5.0 g. of N-(3-amino-3-ethyl-1,5-dioxaspiro[5.5]undecan-9-yl)acetamide in 50 ml. of ethylene dichloride, 2.76 g. of potassium carbonate in 80 ml. of water, 4.38 g. of 4-trifluoromethoxybenzoyl chloride in 50 ml. of ethylene dichloride, and recrystallization twice from chloroform-n-hexane.

9. N-(9-ACETAMIDO-3-METHYL-1,5-DIOXASPIRO[5.5]UNDECAN-3-YL)-4-METHOXYBENZAMIDE, 31.2 g., m.p. 227°–228°C. (sint. 225°C.), was prepared following the procedure described in Example F-1 using 24.23 g. of N-(3-amino-3-methyl-1,5-dioxaspiro[5.5]undecan-9-yl)acetamide in 125 ml. of ethylene dichloride, 26.54 g. of potassium carbonate in 125 ml. of water, 14.9 ml. of 4-methoxybenzoyl chloride in 75 ml. of ethylene dichloride, and recrystallization from acetonitrile.

Following the procedure described in Example F-1 but using molar equivalent quantities of the appropriate 3-R-9-R'-1,5-dioxaspiro[5.5]undecan-3,9-diamine and 4-$Q_2$-benzoyl halide, the compounds of Examples F-10 through F-17 are obtained.

10. N,N'-(3,9-DIETHYL-1,5-DIOXASPIRO[5.5]UNDECAN-3,9-DIYL)BIS(4-TRIFLUOROMETHOXYBENZAMIDE) using 3,9-diethyl-1,5-dioxaspiro[5.5]undecan-3,9-diamine and 4-trifluoromethoxybenzoyl chloride.

11. N,N'-(3-METHYL-1,5-DIOXASPIRO[5.5]UNDECAN-3,9-DIYL)BIS(4-TRICHLOROMETHOXYBENZAMIDE) using 3-methyl-1,5-dioxaspiro[5.5]undecan-3,9-diamine and 4-trichloromethoxybenzoyl chloride.

12. N,N'-(3-METHYL-1,5-DIOXASPIRO[5.5]UNDECAN-3,9-DIYL)BIS[4-(2,2,2-TRIFLUOROETHOXY)BENZAMIDE] using 3-methyl-1,5-dioxaspiro[5.5]undecan-3,9-diamine and 4-(2,2,2-trifluoroethoxy)benzoyl chloride.

13. N,N'-(3-METHYL-1,5-DIOXASPIRO[5.5]UNDECAN-3,9-DIYL)BIS[4-(2-CHLORO-1,1,2-TRIFLUOROETHOXY)BENZAMIDE] using 3-methyl-1,5-dioxaspiro[5.5]undecan-3,9-diamine and 4-(2-chloro-1,1,2-trifluoroethoxy)benzoyl chloride.

14. N,N'-(9-METHYL-1,5-DIOXASPIRO[5.5]UNDECAN-3,9-DIYL)BIS(4-TRIFLUOROMETHOXYBENZAMIDE) using 9-methyl-1,5-dioxaspiro[5.5]undecan-3,9-daimine and 4-trifluoromethoxybenzoyl chloride.

15. N,N'-(3-METHYL-1,5-DIOXASPIRO[5.5]UNDECAN-3,9-DIYL)BIS[4-(1,1,2,2,2-PENTAFLUOROETHOXYBENZAMIDE)] using 3-methyl-1,5-dioxaspiro[5.5]undecan-3,9-diamine and 4-(1,1,2,2,2-pentafluoroethoxy)benzoyl chloride.

16. N,N'-(3-METHYL-1,5-DIOXASPIRO[5.5]UNDECAN-3,9-DIYL)BIS(4-ETHOXYBENZAMIDE) using 3-methyl-1,5-dioxaspiro[5.5]undecan-3,9-diamine and 4-ethoxybenzoyl chloride.

17. N,N'-(3-METHYL-1,5-DIOXASPIRO[5.5]UNDECAN-3,9-DIYL)BIS(4-ISOPROPOXYBENZAMIDE) using 3-methyl-1,5-dioxaspiro[5.5]undecan-3,9-diamine and 4-isopropoxybenzoyl chloride Following the procedure described in Example F-6 but using molar equivalent quantities of the appropriate 3-amino-3-R-9-R'-1,5-dioxaspiro[5.5]undecan-9-yl)acylamide and 4-$Q_2$-benzoyl halide, the compounds of Examples F-18 through F-25 are obtained.

18. N-(3-METHYL-9-PROPIONAMIDO-1,5-DIOXASPIRO[5.5]UNDECAN-3-YL)-4-TRIFLUOROMETHOXYBENZAMIDE using N-(3-amino-3-methyl-1,5-dioxaspiro[5.5]undecan-9-yl)propionamide and 4-trifluoromethoxybenzoyl chloride.

19. N-(9-BUTYRAMIDO-3-METHYL-1,5-DIOXASPIRO[5.5]UNDECAN-3-YL)-4-TRIFLUOROMETHOXYBENZAMIDE using N-(3-amino-3-methyl-1,5-dioxaspiro[5.5]undecan-9-yl)butyramide and 4-trifluoromethoxybenzoyl chloride.

20. N-(9-ISOBUTYRAMIDO-3-METHYL-1,5-DIOXASPIRO[5.5]UNDECAN-3-YL)-4-TRIFLUOROMETHOXYBENZAMIDE using N-(3-amino-3-methyl-1,5-dioxaspiro[5.5]undecan-9-yl)isobutyramide.

21. N-(9-ACETAMIDO-3,9-DIMETHYL-1,5-DIOXASPIRO[5.5]UNDECAN-3-YL)-4-TRIFLUOROMETHOXYBENZAMIDE using N-(3-amino-3,9-dimethyl-1,5-dioxaspiro[5.5]undecan-9-yl)acetamide and 4-trifluoromethoxybenzoyl chloride.

22. N-(9-ACETAMIDO-3,9-DIETHYL-1,5-DIOXASPIRO[5.5]UNDECAN-3-YL)-4-TRIFLUOROMETHOXYBENZAMIDE using N-(3-amino-3,9-diethyl-1,5-dioxaspiro[5.5]undecan-9-yl)acetamide and 4-trifluoromethoxybenzoyl chloride.

23. N-(9-ACETAMIDO-9-METHYL-1,5-DIOXASPIRO[5.5]UNDECAN-3-YL)-4-TRIFLUOROMETHOXYBENZAMIDE using N-(3-amino-9-methyl-1,5-dioxaspiro[5.5]undecan-9-yl)acetamide and 4-trifluoromethoxybenzoyl chloride.

24. N-[9-(4-METHOXYBENZAMIDO)-3-METHYL-1,5-DIOXASPIRO[5.5]UNDECAN-3-YL]-4-TRIFLUOROMETHOXYBENZAMIDE using N-[3-amino-3-methyl-1,5-dioxaspiro[5.5]undecan-9-yl]-4-methoxybenzamide and 4-trifluoromethoxybenzoyl chloride.

25. N-[9-(4-DIFLUOROMETHOXYBENZAMIDO)-3-METHYL-1,5-DIOXASPIRO[5.5]UNDECAN-3-YL]-4-TRIFLUOROMETHOXYBENZAMIDE using N-(3-amino-3-methyl-1,5-dioxaspiro[5.5]undecan-9-yl)-4-difluoromethoxybenzamide and 4-trifluoromethoxybenzoyl chloride.

The antifertility activity of the compounds of the invention was determined by the following standard test procedure which involves female rats which are medicated prior to, during and after the mating period. The rats are autopsied on the fourteenth post mating day and uteri are examined for evidence of pregnancy. The procedural details are as follows: A colony of sexually mature female rats of the Sprague-Dawley strain weighing 200–300 gms. are maintained on routine laboratory care. Daily vaginal smears are examined to record the cyclic characteristics of each rat. A given test is composed of rats which have exhibited a minimum of three coincidental estrus cycles. Three days prior to an expected estrus the rats to be placed on test are grouped, housed individually and placed on medication. The medication consists of a test compound, prepared as a solution or suspension in a suitable vehicle, administered orally via stomach tube once daily for a total of eight medications in a ten day period (Sunday medications are omitted). One group received only the vehicle in a like manner to serve as a control. Late in the afternoon of the day preceding the expected estrus a mature proven fertile male is housed with each female overnight. The following morning all males are removed and a vaginal smear of each female is examined for the presence of spermatozoa as evidence that insemination has occurred. Medication of all inseminated rats is continued through the seventh post insemination day. The rats are autopsied seven days after the last medication and the uteri removed and examined for evidence of pregnancy. The number of implantation sites, number of resorption sites, total number of fetuses and the number of viable fetuses are recorded. When tested by this procedure, the compounds of the invention were found to have antifertility activity at dose levels ranging from about 25 to 400 mg. per kg. per day. Illustrative compounds of the invention found to have antifertility activity as determined by the above procedure include: N,N'-(3-methyl-1,5-dioxaspiro[5.5]undecan-3,9-diyl)bis(4-trifluoromethoxybenzamide, N,N'-(3-methyl-1,5-dioxaspiro[5.5]undecan-3,9-diyl)bis(4-methoxybenzamide), N,N'-(3-ethyl-1,5-dioxaspiro[5.5]undecan-3,9-diyl)bis(4-trifluoromethoxybenzamide), N-(9-acetamido-3-methyl-1,5-dioxaspiro[5.5]undecan-3-yl)-4-trifluoromethoxybenzamide and N-(9-acetamido-3-ethyl-1,5-dioxaspiro[5.5]undecan-3-yl)-4-trifluoromethoxybenzamide.

The actual determination of the numerical antifertility data definitive for a particular compound is readily obtained by standard test procedures, referred to above, by technicians versed in endocrinological test procedures, without any need for any extensive experimentation.

The compounds of the invention can be prepared for use by conventional pharmaceutical procedures: that is, by dissolving or suspending them in a pharmaceutically acceptable vehicle, e.g., aqueous alcohol, glycol, oil solution, or oil-water emulsion, for parenteral or oral administration; or by incorporating them in unit dosage form as tablets or capsules for oral administration either alone or in combination with conventional adjuvants, e.g., calcium carbonate, starch, lactose, talc, magnesium stearate, gum acacia, and the like.

We claim:

1. A compound of the formula

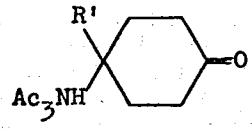

where R' is hydrogen or lower-alkyl, $Ac_3$ is 4-$Q_1$-benzoyl and $Q_1$ is lower-alkoxy or polyhalo-lower-alkoxy.

2. A compound according to claim 1 where R' is hydrogen.

3. A compound according to claim 2 where $Ac_3$ is 4-methoxybenzoyl.

4. A compound according to claim 2 where $Ac_3$ is 4-trifluoromethoxybenzoyl.

* * * * *

UNITED STATES PATENT AND TRADEMARK OFFICE
CERTIFICATE OF CORRECTION

PATENT NO. : 3,960,945
DATED : June 1, 1976
INVENTOR(S) : George Y. Lesher, Karl O. Gelotte and Alexander R. Surrey It is certified that error appears in the above-identified patent and that said Letters Patent are hereby corrected as shown below:

Title page [54], "4-[-" should read -- 4-[4- --.

Column 1, line 2, "4-[-" should read -- 4-[4- --.

Column 1, line 34, "produces" should read -- produce --.

Column 5, line 68, "R40" should read -- R' --.

Column 6, line 4, "2-nnitro-" should read -- 2-nitro- --.

Column 6, line 6, "-9R'-" should read -- -9-R'- --.

Signed and Sealed this

Nineteenth Day of October 1976

[SEAL]

Attest:

RUTH C. MASON
Attesting Officer

C. MARSHALL DANN
Commissioner of Patents and Trademarks